United States Patent [19]

Fukushima et al.

[11] 4,337,315

[45] Jun. 29, 1982

[54] CONTINUOUS FERMENTOR AND REACTOR

[75] Inventors: Susumu Fukushima, Toyonaka; Hideaki Munenobu, Ibaragi; Kazuhiro Yamade, Wakayama, all of Japan

[73] Assignees: Tokyo Kikakikai Co., Ltd., Tokyo; Kansai Chemical Engineering Co., Ltd., Hyogo; Takara Shuzo Co., Ltd., Kyoto, all of Japan

[21] Appl. No.: 198,090

[22] Filed: Oct. 17, 1980

[30] Foreign Application Priority Data

Mar. 4, 1980 [JP] Japan .................................. 55-27724
Jul. 8, 1980 [JP] Japan .................................. 55-93502

[51] Int. Cl.³ .............................................. C12M 1/04
[52] U.S. Cl. .................................. 435/313; 261/79 A; 422/193; 422/195; 435/304; 435/314; 435/315; 435/316; 435/813; 435/818; 435/819
[58] Field of Search .............. 435/313, 314, 315, 316, 435/304, 813, 818, 819; 422/193, 195; 261/79 A

[56] References Cited

U.S. PATENT DOCUMENTS 3,251,653  5/1966  Aditya .................................. 422/193
3,743,582  7/1973  Kitai et al. ...................... 435/313 X Primary Examiner—Robert J. Warden
Attorney, Agent, or Firm—Sughrue, Mion, Zinn, Macpeak & Seas

[57] ABSTRACT

A continuous fermentor or reactor and process using the reactor for producing ethanol including at least two vertically arranged unit reactors each having an open top cone which is connected to an inverted open bottom cone by a short cylinder greater in diameter than the two cones. The lowest unit reactor is connected to a gas supply member and a liquid introducing pipe and the highest unit reactor is connected to a gas separator and a mash discharge pipe. Inert gas introduced into the bottom unit produces both upward and downward flows in each unit.

8 Claims, 7 Drawing Figures

CONTINUOUS FERMENTOR AND REACTOR

BACKGROUND OF THE INVENTION

1. Field of the Invention

The invention relates to an apparatus for fermentation or reaction wherein microorganism cells or catalyst particles suspended in liquid are brought into contact with a gas phase.

The invention further relates to a process for continuously or batchwise producing ethanol by fermentation using disaccharide, monosaccharide, or the mixture thereof as a starting material.

2. Description of the Prior Art

One of the inventors of the present invention previously proposed a reactor of the same general type in which two cones are coupled at their bases. As described in Japanese Patent Application Nos. 92774/77 and 76564/79, the reactor is useful not only for immobilization of enzymes and oxidation with immobilized enzymes but also for anaerobic fermentation.

In later research on the large-scale and continuous conversion of sugar to alcohol, considered to be a potential energy substitute, the present inventors have found that a multi-stage bioreactor composed of vertically connected unit reactors each having two cones coupled at their bases is a very effective continuous fermentor.

SUMMARY OF THE INVENTION

In accordance with the teachings of the present invention, there is provided a multi-stage bioreactor for converting sugar to alcohol including at least two vertically arranged unit reactors each including an open top case connected to an inverted open bottom cone by a short cylinder greater in diameter than the top and bottom cones, a gas disperser and a liquid introducing pipe connected to a lowest one of the reactors, and a gas separator and mash discharge pipe connected to a highest one of the unit reactors. A heating or cooling jacket can, if desired, be disposed around the stack of unit reactors. The gas disperser preferably has a gas supply chamber which is separated from the lowest unit reactor by a gas disperser.

Yet further, the invention can be practiced by an ethanol production process from saccharide substrates such as glucose, blackstrap molasses, and sugar syrup in a fermentation reactor which is constructed of at least two vertically arranged unit reactors each having an open top cone connected to an inverted open bottom cone by a short cylinder which is greater in diameter than either of the top and bottom cones. By introducing a gas phase of inert gas bubbles into the reactor through the gas disperser, a mash composed of liquid substrates and yeast cells is produced in both upward and downward streams in each stage thereby creating a continuous liquid flow which causes mixing of the liquid substrate contained therein with the number of yeast cells in the various units gradually decreasing as the solution ascends to higher units. Carbon dioxide and a part of the ethanol are transferred from the liquid phase to the inert gas bubbles and the bubbles are discharged from a top of the reactor during the process allowing an unrefined product to flow out. Yeast is separated from the unrefined product and the separated solution is distilled to thereby produce ethanol.

BRIEF DESCRIPTION OF THE DRAWINGS

Preferred embodiments of the invention will be hereafter described with reference to the accompanying drawings, in which.

DESCRIPTION OF THE PREFERRED EMBODIMENTS

Figure 1:
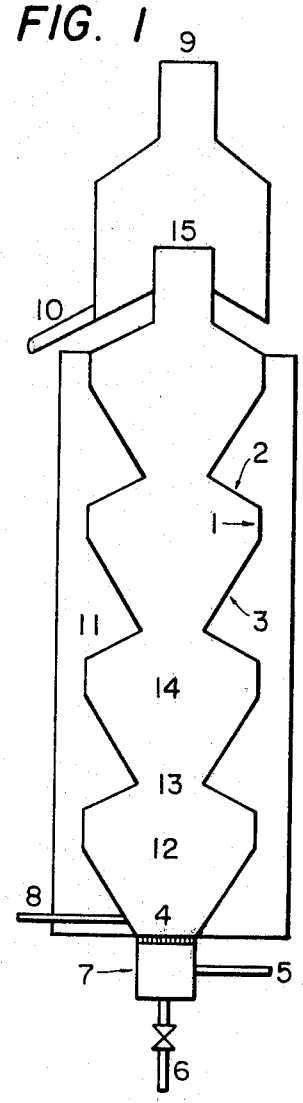
FIG. 1 is a longitudinal cross section of a continuous fermentor constructed in accordance with the teachings of the invention.

First, with reference to FIG. 1, each unit reactor is provided with a top cone 2 which is connected to an inverted bottom cone 3 by a short cylinder 1 positioned slightly above the middle portion of the unit and being of greater diameter than the two cones. The bottom of the lowest unit is connected to a gas disperser 4 composed of a sintered or porous plate. The disperser is connected to a gas supply chamber 7 equipped with a gas supply pipe 5 and a drain pipe 6. One or more liquid supply pipes 8 are connected tangentially to a portion of the inverted cone 3 of the lowest unit reactor close to the bottom thereof. The top of the fermentor 15 is connected to a gas outlet 9 and a liquid mash discharge pipe 10. Each unit reactor is provided with a cooling or heating jacket 11.

Figure 2:
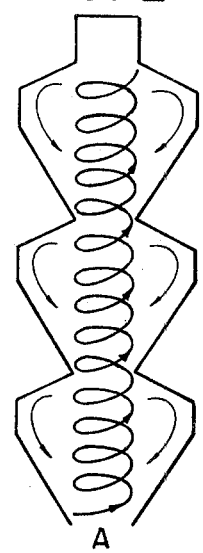
FIG. 2 is an explanatory diagram illustrating the behavior of the gas liquid mixture in the fermentor.

A liquid substrate supplied to the lowest unit in tangential direction of the wall through the pipe 8 forms a vortex that ascends up in the column of the unit in the direction indicated by arrow A of FIG. 2. As the substrate ascends higher, the diameter of the vortex increases and the flow rate of the liquid decreases. The decrease in the flow rate is held to a minimum by bubbles of a gas supplied through the pipe 5 and which pass through the disperser 4 ascending the belly 12 of the reactor.

Part of the microorganism cells and liquid as well as the small gas bubbles descend along the inner walls of the top cone 2. Upon reaching the bottom cone, the descending mass changes its direction and ascends the reactor because of the ejector effect, that is, the upward current of gas bubbles has a higher pressure than the downward current. The remaining part of the liquid and microorganism cells as well as the gas bubbles pass through the neck 13 of the unit reactor entering the unit reactor 14 upwardly adjacent to the lowest unit. In that reactor, the behavior therein is the same as in the lowest unit. Ascending to the top of the fermentor 15 through a series of unit reactors in the manner described, the mash is separated from the gas bubbles and supplied to a solid-liquid separator through the pipe 10. The mash in each stage of the fermentor is effectively fluidized by a stirring gas. To maintain the steady fermentation process, the heat of fermentation evolved is transferred through the cooling jacket 11. The stirring gas may be one component of the substrate or it may be an inert gas.

One advantage of the invention is that none of the necks 13 can be filled with gas bubbles, which action could disconnect the fluid flowing through one stage from that flowing through another. Instead, the fluid flowing through consecutive stages forms a continuous stream that carries the suspended solid particles toward the top of the fermentor. The continuity in the fluid flowing through adjacent stages not only facilitates steady operation of the fermentor but it is also useful in performing operations that cannot be performed without the presence of liquid on and within the suspended solid particles.

Figure 4:
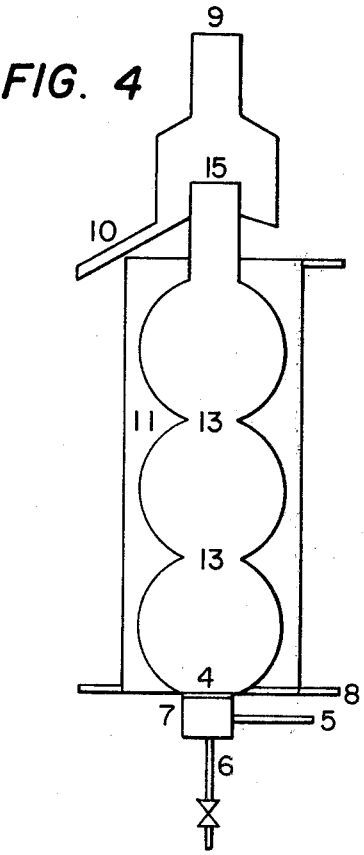
FIG. 4 shows another embodiment of the fermentor of this invention which includes a plurality of spherical unit reactors.
Figure 3:
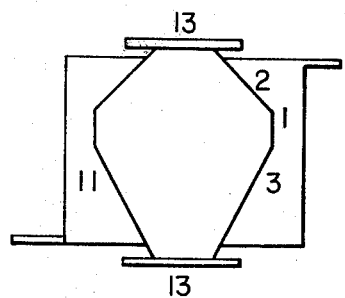
FIG. 3 is a cross-sectional view of a unit reactor used in the fermentor of the invention.

The continuous three-phase fermentor illustrated in FIG. 1 is composed of a plurality of unit reactors as shown in FIG. 3 serially connected one on top of another or provided integrally. Each unit may be spherical as shown in FIG. 4 instead of a combination of two cones joined at their bases. Adjacent units must be connected with a short neck because, if they are connected with a long pipe, combined gas bubbles would fill the pipe to prevent the formation of a continuous stream. It is to be understood that the liquid substrate need not be supplied to the lowest unit reactor.

The foregoing description concerns the application of the invention to fermentation but it should be understood that the apparatus of the invention is also applicable to other reactions. Next, an application of the invention to a process for producing ethanol will be described.

Generally, fresh yeasts produce ethanol at a higher fermentation rate and have a heavier specific gravity than less fresh yeasts which produce ethanol with a significantly lower fermentation rate with a lighter specific gravity.

Figure 5:
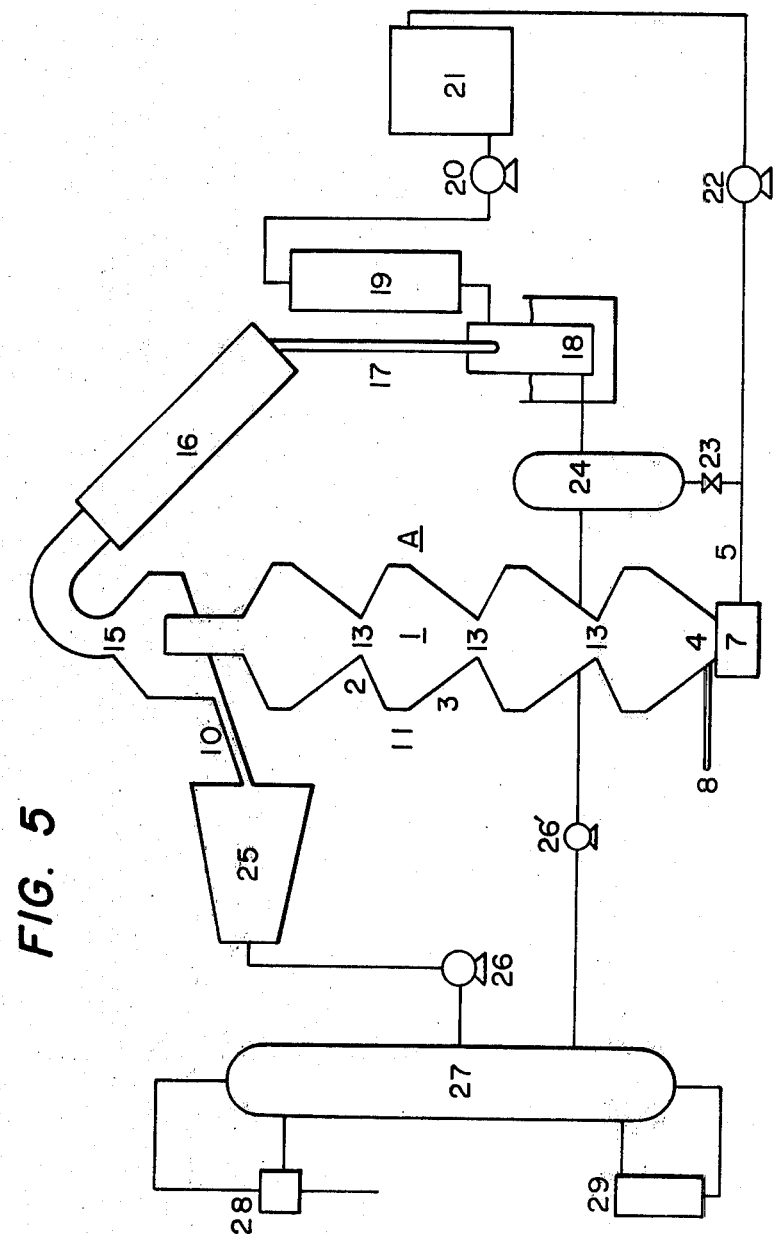
FIG. 5 is a cross-sectional view of a bioreactor for producing ethanol according to the process of the invention.

A multi-stage, three phase fluidized bioreactor constructed as illustrated in FIG. 5 provides quite good mixing of the liquid substrate solution in each stage and, since the solution in each stage flows continuously, the amount of yeast decreases as the solution ascends higher from one stage to the next higher stage. Simultaneously, old yeast cells are separated from the gas together with the solution and discharged out from upper end of the reactor. As no blockage or plug-up of the reactor by yeast cells can take place within the cones of the reactor, removal of fermentation heat is easily attained so that the fermentation process is carried out in an almost stationary state.

In FIG. 5, the continuous fermentor A includes, as in the previously described embodiment, vertically connected units or cones each of which has a straight short cylinder 1, a top cone 2, and a bottom cone 3. Air or nitrogen gas is introduced into the fermentor through a gas disperser 4 which is connected to a gas supply chamber 7 by a gas-supply pipe 5 and a substrate solution is introduced via the bottom liquid-supply pipe 8. The gas and the solution are vigorously mixed in each unit and at necks 13 dispersion is accelerated due to an ejector effect.

The gas and the mash ascend while the fermentation process proceeds entering the gas-liquid separator 15 located at the top of the fermentor. Evaporated ethanol and water vapor accompanied by nitrogen and carbon dioxide gas, air and carbon dioxide gas or only carbon dioxide gas are condensed in condenser 16 and a condensed aqueous ethanol solution is carried into tank 18 through pipe 17 and is conveyed by a pump 26' to distillation tower 27. The gas separated from the aqueous ethanol solution is recycled by a press-sending system including a buffer tank 19, an air pump 20, a buffer thank 21, a gas pump 22, a valve 23, and a bomb 24 connected to a gas-supply chamber 7 of the fermentor A.

The fermentation solution conveyed via the discharge pipe 10 is separated into yeasts and ethanol solution from the mash by a solid-liquid separator 25 after which the solution is conveyed by a pump 26 to a distillation tower 27 including a condenser 28 and a reboiler 29 where it is concentrated.

Figure 6:
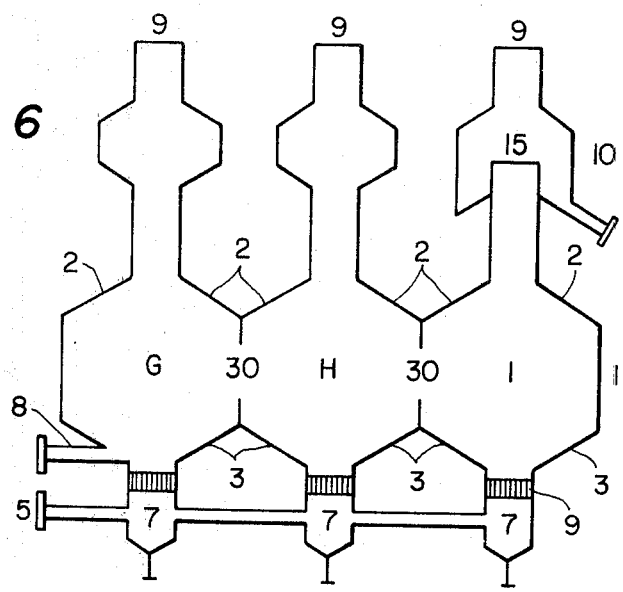
FIG. 6 is a cross-sectional view of a lateral continuous reactor.

In the embodiment shown in FIG. 6, three reactor units are connected laterally in sequence. Each unit has a gas outlet 9 at the top and a gas supply chamber 7 at the bottom of its tank. The feed solution is supplied to the bottom of the first unit G by the liquid supply pipe 8 and the product solution is delivered from the outlet 10 located at the top of the final unit I. The solution or mash is conveyed through units G and H to unit I while it is mixing. If solid catalyst particles or biocatalyst particles are used, there may be a uniform distribution of particles for each unit at the connectors 30 between units as the solution is conveyed from unit G to unit H to unit I. Gas is supplied in each unit. Thus, the pressure drop is small in comparison with the vertical multistage bioreactor as shown in FIGS. 1 and 5.

Figure 7:
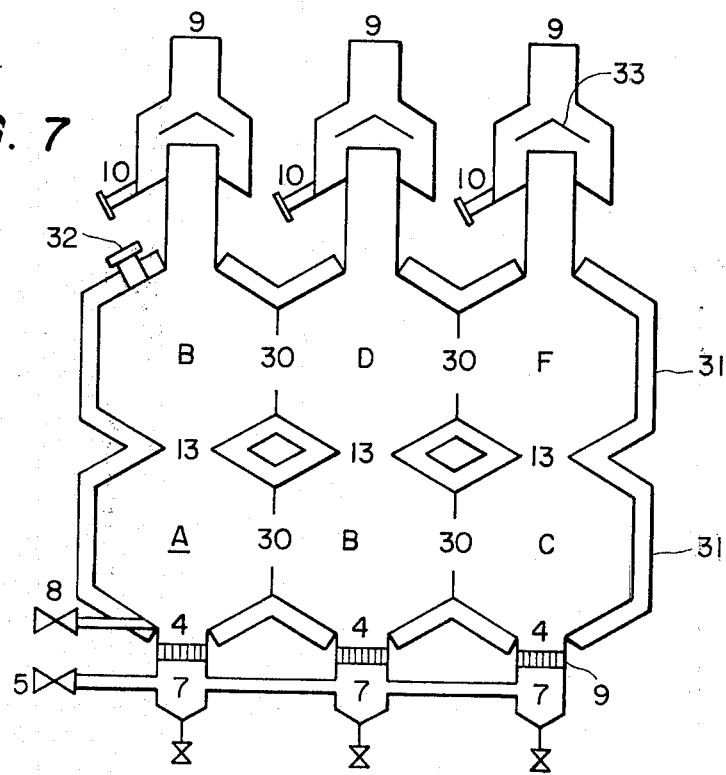
FIG. 7 is a cross-sectional view of vertical and lateral reactors.

FIG. 7 illustrates vertically and laterally arranged double conical bioreactor units. The biocatalysts particles are charged from the inlet 32 located at the upper part of the first column and the product solution is withdrawn through the outlet 10 located at the top of each column. The reactor temperature in each bioreactor unit is controlled through the use of the jacket 31.

The present invention will now be further described with reference to specific examples.

EXAMPLE 1

Blackstrap molasses was used as a starting material and the reaction proceeded as illustrated below with the aid of yeast.

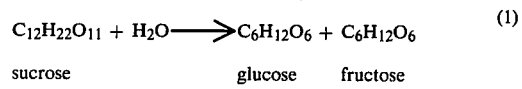
(1)

sucrose            glucose    fructose

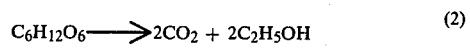
(2)

Carbon dioxide as an inert gas was introduced into a three-stage, upward-and-downward conical bioreactor constructed as described above, having an equivalent volume per stage of 700 ml, through the bottom end via a disperser at a rate of 400 N cm$^3$/min. Then, sterilized molasses containing 0.24 gmole/l sucrose, 0.33 gmole/l glucose, and 0.32 gmole/l fructose and having a pH of 4.5 at 30° C. was introduced thereinto through the lower end at a flow rate of 2.5 cm$^3$/min. When the solution and the gas filled the second stage bioreactor unit, 100 g (dry weight, 33 g) of living cells in the form of Saccharomyces cerevisiae was charged one time through an inlet.

After about 40 hours, the alcohol concentration attained a pseudo-stationary state. The concentrations of cells in respective stages of the reactor are shown below.

TABLE 1

| Stage | Days Elapsed | |
|---|---|---|
| | 7 Days | 12 days |
| Top Stage | $4.0 \times 10^7$ cell/ml | $6.4 \times 10^7$ cell/ml |
| Middle Stage | $9.9 \times 10^7$ cell/ml | $7.7 \times 10^7$ cell/ml |
| Bottom Stage | $1.1 \times 10^8$ cell/ml | $8.6 \times 10^7$ cell/ml |

As is shown above, the concentration of yeast cells in the upper stage is smaller than that in the lower stage. Although the concentration of yeast cells decreased after 12 days as compared with that after 7 days, the ethanol concentration in the solution was 5.5 (W/V) % and the gas contained 0.6–0.7 (W/V) % ethanol with both being almost constant. This fact shows that the ethanol-producing activity of new cells increased while the old cells were discharged. A 25-day continuous run was smoothly carried out with no operational difficulties.

EXAMPLE 2

Potatoes were sliced and liquefied using α-amylase and glucoamylase enzyme to saccharify the mash. A sugar solution containing glucose derived from potatoes in a concentration of 1.2 gmole/l and small amounts of ammonium sulfate, phosphate, magnesium sulfate and vitamins were subjected to the same procedures as described above using the same yeast. As a result, a solution was obtained containing 5.1 (W/V) % ethanol.

The continuous three-phase reactor in FIG. 6 is composed of a plurality of unit reactors arranged laterally. An open part of a short cylinder 1 greater in diameter than the top and bottom cones in the first unit reactor is connected with the short cylinder of the adjacent second unit reactor. Thus, the liquid or slurry product transfers from the first unit reactor to the second. The pressure drop in this lateral arrangement is small in comparison with that in a vertical arrangement.

The continuous three-phase reactor in FIG. 7 is vertically and laterally composed of a plurality of unit reactors.

EXAMPLE 3

Immobilized Saccharomyces cerevisiae cell gel particles which were entrapped with polyarcylamide were used as biocatalyst particles instead of intact cells. Nitrogen gas as the inert gas was fed into a three-unit bioreactor as used in Example 1 through the gas disperser at 800 N cm$^3$/min. Sterilized molasses containing 0.45 gmole/l sucrose, 0.33 gmole/l glucose and 0.32 gmole/l fructose was fed at 0.74 cm$^3$/min. The reaction was operated at a temperature of 30° C. and at a pH of 4.88.

In the bioreactor, the number and total volume of immobilized Saccharomyces cerevisiae cells and the volume of the gel were $2.57 \times 10^5$ and 225 cm$^3$, respectively. The immobilized cells were not released from the bioreactor by a net located at the liquid outlet of the bioreactor. The effluent solution from the bioreactor contained 60 g/l ethanol and 0.32 gmole/l monosaccharide after 25 days. Also, ethanol from discharged gas from the bioreactor flowed at the rate of 14 g/day.

EXAMPLE 4

Immobilized Saccharomyces carlsbergensis cell gel particles which were entrapped with polyacrylamide were used and the continuous reactor was the type as shown in FIG. 5. Nitrogen gas was fed through the gas disperser in each unit reactor at 100 N cm$^3$/min. The feed solution contained 0.65 gmole/l glucose and $10^{-3}$ gmole/l magnesium sulfate with a phosphate buffer at pH 4.5. This solution was fed to the first unit reactor at a rate of 0.1 cm$^3$/min. The total volumes of solution and immobilized cells particles were 243 and 24 cm$^3$, respectively. The reaction was operated at 30° C. The effluent solution from the final unit reactor contained 60 g/l ethanol. When the feed solution had a high glucose content, much ethanol was transferred from the solution to the gas phase. The solution containing 1.2 gmole/l glucose was fed at 0.1 cm$^3$/min. The total production rate of ethanol was 15 g/day. Half of this rate was obtained from the effluent solution in the final unit reactor.

What is claimed is:

1. A continuous reactor comprising at least two unit reactors each comprising an open top cone-shaped member;
   an inverted open bottom cone-shaped member;
   a cylinder, said top and bottom members being connected to said cylinder at opposite ends thereof;
   a gas supply member and a liquid introducing pipe connected to a lowest unit reactor; and
   a gas separator and a liquid product or slurry product discharge pipe connected to a highest unit reactor.

2. The continuous reactor of claim 1 wherein said unit reactors are arranged vertically.

3. The continuous reactor of claim 1 wherein said unit reactors are arranged laterally.

4. The continuous reactor of claim 1 comprising at least two additional unit reactors, and said unit reactors being arranged both vertically and laterally.

5. The continuous reactor of claim 3 or 4 wherein said cylinder has an open part of which is connected to an adjacent laterally-arranged cylinder for discharging a liquid or slurry product from one unit reactor to a lateral unit reactor.

6. The continuous reactor of claim 1 further comprising a jacket disposed around said unit reactors for conveying a temperature-changing fluid.

7. The reactor of claim 1 wherein said supply member comprises a gas supply chamber and a gas disperser disposed between said gas supply chamber and said lowest unit reactor.

8. The continuous reactor of claim 1 wherein said cylinder has a diameter greater than a maximum diameter of said top and bottom cone-shaped members, said top and bottom cone-shaped members being connected to an inner wall of said cylinder at opposite ends thereof.

* * * * *